United States Patent [19]

Indravudh

[11] Patent Number: 5,197,322
[45] Date of Patent: Mar. 30, 1993

[54] PRESSURE RESERVOIR FILLING PROCESS FOR AN IMPLANTABLE MEDICATION INFUSION PUMP

[75] Inventor: Virote Indravudh, Saugus, Calif.

[73] Assignee: Minimed Technologies, Ltd., Sylmar, Calif.

[21] Appl. No.: 619,858

[22] Filed: Nov. 29, 1990

[51] Int. Cl.⁵ .................. G01F 25/00; A61M 37/00
[52] U.S. Cl. .......................................... 73/3; 604/141
[58] Field of Search .................. 73/4 R, 3, 865.6; 604/140, 141; 417/394

[56] References Cited

U.S. PATENT DOCUMENTS

| | | | |
|---|---|---|---|
| 3,164,979 | 1/1965 | Siegel | 73/4 R |
| 3,782,168 | 1/1974 | Wailes | 73/4 R |
| 4,189,936 | 2/1980 | Ellis | 73/4 R |
| 4,370,983 | 2/1983 | Lichtenstein | 128/630 |
| 4,373,527 | 2/1983 | Fischell | 604/891.1 |
| 4,537,058 | 8/1985 | Luper | 73/3 |
| 4,573,994 | 3/1986 | Fischell et al. | 604/48 |
| 4,664,635 | 5/1987 | Hermann | 73/4 R |
| 4,673,391 | 6/1987 | Kondo et al. | 604/141 |
| 4,955,861 | 9/1990 | Enegren et al. | 604/141 |
| 5,061,242 | 10/1991 | Sampson | 604/141 |

FOREIGN PATENT DOCUMENTS 8106409  10/1982  France .................. 73/4 R

Primary Examiner—Hezron E. Williams
Assistant Examiner—George Dombroske
Attorney, Agent, or Firm—Stuart O. Lowry; Leslie S. Miller

[57] ABSTRACT

An improved process and related apparatus are provided for filling a pressure reservoir of an implantable medication infusion pump with a selected pressure fluid, wherein the pressure reservoir is separated by a movable wall from an adjacent medication chamber. The improved filling process includes vacuum-draw filling of the pressure reservoir with relatively purified pressure fluid in liquid state. The specific quantity of pressure fluid within the pressure reservoir is thereafter calibrated by filling the adjacent medication chamber with a calibration fluid at a predetermined positive pressure, thereby expelling excess pressure fluid from the pressure reservoir. The pressure reservoir is then sealed and the performance characteristics thereof are tested under simulated implantation conditions to confirm the capability of the pressure reservoir to maintain medication within the medication chamber under substantially constant pressure conditions.

23 Claims, 3 Drawing Sheets

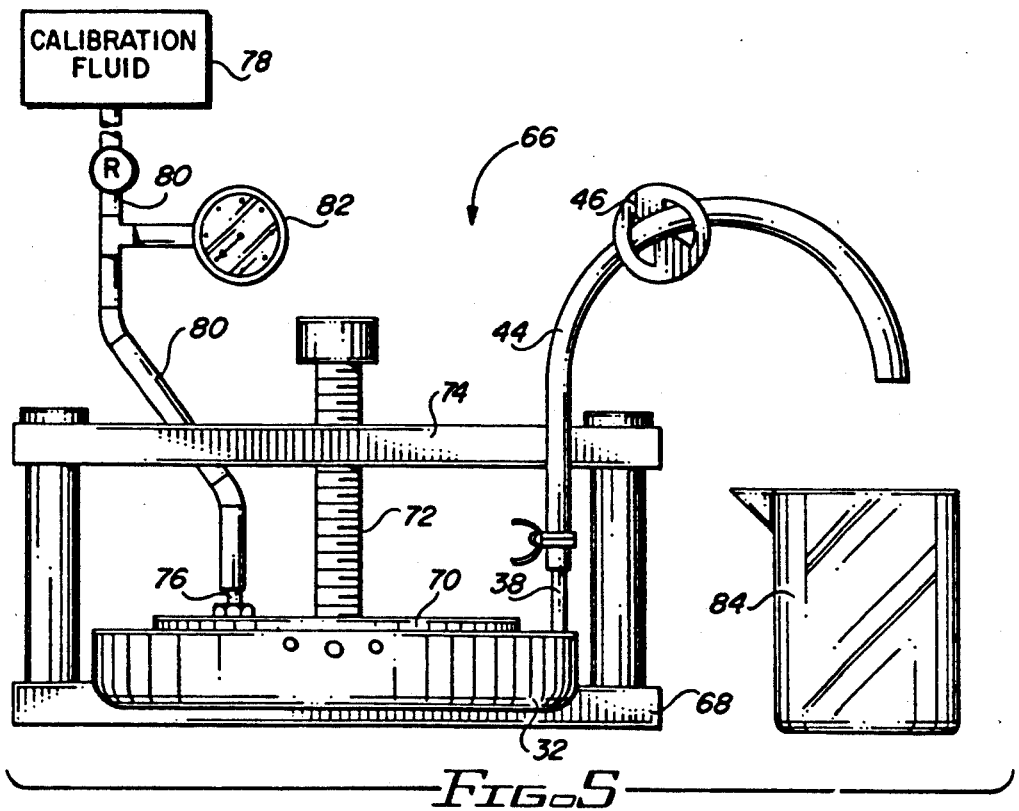
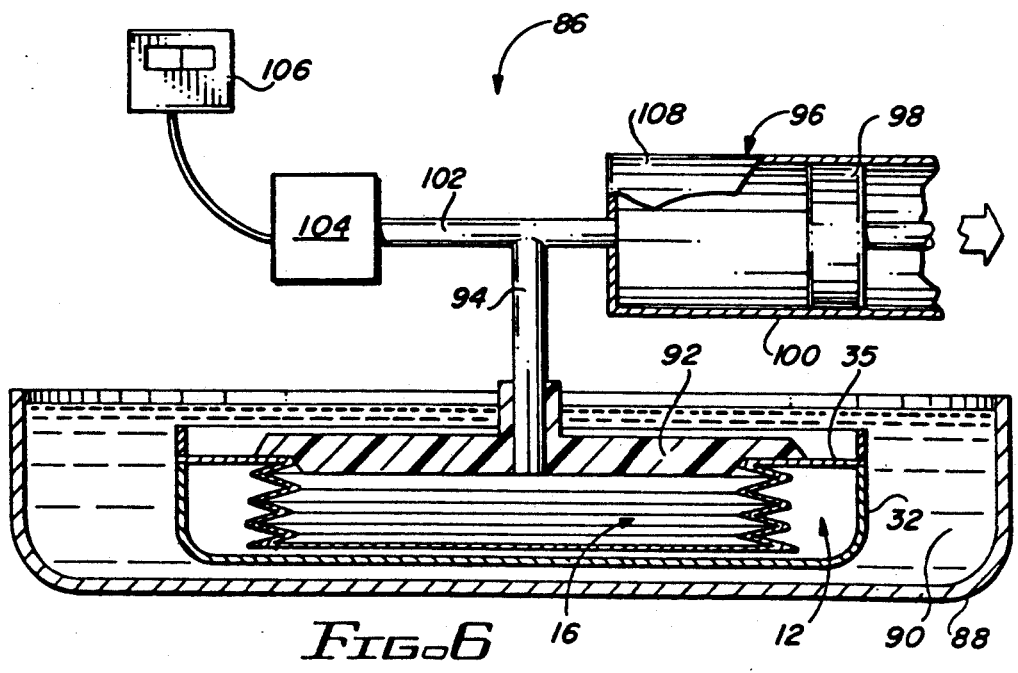

PRESSURE RESERVOIR FILLING PROCESS FOR AN IMPLANTABLE MEDICATION INFUSION PUMP

BACKGROUND OF THE INVENTION

1. Field of the Invention

This invention relates generally to an improved process and related apparatus for use in filling the pressure reservoir of an implantable medication infusion pump with a selected pressure fluid, and more particularly to an improved pressure reservoir filling process and related process stations for filling the pressure reservoir with a calibrated quantity of relatively purified pressure fluid, and for testing the performance characteristics of the pressure reservoir under simulated implantation conditions.

Medication infusion pumps are generally known in the art for use in delivering a selected medication to a patient in a scheduled or preprogrammed manner. In recent years, such infusion pumps have been developed in compact form adapted for direct implantation into the body of a patient, and to deliver a specific medication such as insulin to the patient in discrete dosages over an extended period of time. An implanted infusion pump of this general type typically includes an internal medication chamber for receiving and storing a supply of the selected medication in liquid form, with the medication being subjected to a predetermined storage pressure to insure accurate and repeatable delivery conditions through the use of a miniature pump and associated programmable control means. In many cases, the storage pressure is desirably less than ambient body pressure to prevent undesired leakage of the medication from the medication chamber into the body of the patient, and to thereby positively prevent accidental overdose during certain failure modes. For one illustrative example of an implanted medication infusion pump of this general type, see U.S. Pat. No. 4,573,994, to Fischell.

In the past, the medication within the pump medication chamber has been subjected to the desired storage pressure by forming at least a portion of the medication chamber as a movable wall shared with an adjacent pressure reservoir charged with a selected pressure fluid. More particularly, the pressure fluid has comprised a selected fluorocarbon or the like which undergoes liquid-vapor change of state at normal body temperature to appropriately expand or contract the pressure reservoir in a manner acting through the movable wall to maintain the medication chamber under substantially constant pressure conditions.

As the medication chamber is filled, the pressure fluid undergoes significant state change to the liquid phase to reduce the volumetric size of the pressure reservoir. Conversely, as the medication is delivered in doses to the patient, the pressure fluid progressively undergoes state change to the vapor phase to maintain the medication under substantially constant pressure. Freon 113 has been used as the pressure fluid to maintain the medication at a slight negative or subambient pressure in response to normal patient body temperature and altitudinal variations up to 8,500 feet above sea level.

While Freon 113 and similar fluorocarbon materials theoretically maintain the medication under controlled pressure conditions for accurate and repeatable administration to the patient, the actual performance of such fluorocarbon materials is easily and significantly altered in the presence of contaminants within the pressure reservoir. More specifically, small quantities of contaminating air and water are readily ingested by the fluorocarbon material, with the result that the contaminated pressure fluid within the pressure reservoir often does not maintain the medication at the predetermined and substantially constant design pressure.

The impact of such contaminants can be especially pronounced when the medication chamber is completely or nearly filled with liquid medication, such that the pressure reservoir has a substantially minimum volumetric size with the pressure fluid in a predominantly liquid phase state. To avoid or minimize the effects of such contaminants, the medication chamber has typically been filled to a level significantly below the maximum chamber volume or capacity. Unfortunately, this approach fails to optimize the medication-containing capacity of the implantable infusion pump, resulting in a requirement for refilling of the medication chamber at shorter intervals. Alternatively, comparatively larger infusion pumps having larger capacity medication chambers have been needed to increase the medication-containing capacity of the implantable pump.

Too much fluid in the pressure chamber can cause problems with nucleation of the fluid when the reservoir is fully filled to capacity, reducing the volume of the pressure chamber to its minimum size. On the other hand, too little fluid in the pressure reservoir will not provide sufficient pressure (be it either positive or negative) on the medication chamber wall shared in common with the pressure chamber. Thus, it would be highly desirable to somehow calibrate the amount of fluid sealed in the pressure reservoir.

There exists, therefore, a significant need for improved processes and related apparatus for filling the pressure reservoir of an implantable medication infusion pump with a specific or calibrated quantity of a selected and substantially contaminant-free pressure fluid. There exists further a need for a method and related apparatus for verifying proper operation of the pressure fluid during simulated implantation conditions to maintain liquid medication under substantially constant pressure, prior to implantation surgery. The present invention fulfills these needs and provides further related advantages.

SUMMARY OF THE INVENTION

In accordance with the invention, an improved process is provided for filling and testing the pressure reservoir of an implantable medication infusion pump with a selected pressure fluid, such as a fluorocarbon in liquid-gas phase. The pressure reservoir comprises a substantially closed volume which is expansible and defines a movable wall shared with an adjacent medication chamber disposed within the pump and adapted to receive a supply of a selected medication in liquid form for dispensing to a patient.

The pressure reservoir expands or contracts through appropriate liquid-gas phase shift to maintain the medication within the medication chamber under predetermined and substantially constant pressure conditions. The improved process of the present invention provides for filling of the pressure chamber with a calibrated quantity of the pressure fluid substantially without introduction of undesired contaminants, and for subsequent performance testing of the pressure reservoir to verify proper operation thereof.

In accordance with the preferred form of the present invention, a selected pressure fluid such as a fluorocarbon is initially subjected first to passage through a sieve to remove entrained moisture from the pressure fluid in liquid phase. The pressure fluid is then subjected to a boiling step to remove entrained air from the pressure fluid in liquid phase. The thus-purified, substantially contaminant-free pressure fluid is then drawn by vacuum into the pressure reservoir of a pump reservoir subassembly which is supported at a filling station. During vacuum-draw filling of the pressure reservoir, the movable wall is displaced and held at a position defining a substantially minimum volume configuration for the pressure reservoir.

The subassembly with the thus-filled pressure reservoir is placed into a calibration station whereat the adjacent medication chamber is closed and filled with a selected calibration fluid gas at a predetermined positive pressure, such as about 10 psi. The pressure reservoir is opened to permit the positive pressure in the medication chamber to expel an excess portion of the pressure fluid from the pressure reservoir. The residual pressure fluid within the pressure reservoir is thus controlled or calibrated in a precise manner.

The pressure reservoir is closed and sealed, and the pump subassembly is immersed within a controlled temperature bath at substantially atmospheric pressure to simulate normal operational conditions when the fully assembled pump is implanted into the body of a human patient. The medication chamber is filled with a selected liquid such as water at normal body temperature and sealed. A vacuum draw piston assembly is then manipulated to withdraw a small quantity of the liquid from the medication chamber thereby permitting the pressure fluid to initiate phase change to the gaseous state and thus subject the medication to a selected pressure. The quantity of fluid withdrawn to achieve a target design pressure is monitored to confirm proper operational performance of the pressure reservoir.

Other features and advantages of the present invention will become more apparent from the following detailed description taken in conjunction with the accompanying drawings which illustrate, by way of example, the principles of the invention.

DESCRIPTION OF THE DRAWINGS

These and other advantages of the present invention are best understood with reference to the drawings, in which:

FIG. 5 is a somewhat schematic diagram of a calibration station for calibrating the quantity of pressure fluid within the pressure reservoir; and FIG. 6 is a somewhat schematic diagram illustrating a performance test station for determining pressure reservoir performance during simulated implantation conditions.

DETAILED DESCRIPTION OF THE PREFERRED EMBODIMENT

As shown in the exemplary drawings, an improved process and related apparatus are provided for use in filling a pressure reservoir 12 of an implantable medication infusion pump 14. The improved reservoir filling process and the related apparatus used therewith permits the pressure reservoir 12 to be filled with a calibrated quantity of a selected pressure fluid which can be subjected to performance testing under simulated implantation conditions to verify proper design operation in maintaining a selected medication within a medication chamber 16 under substantially constant pressure conditions.

Figure 1:
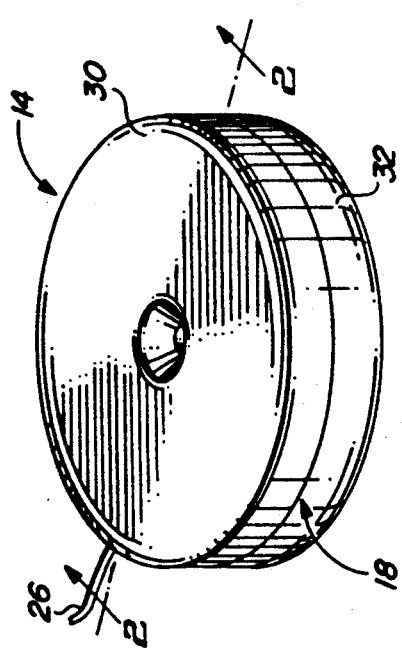
FIG. 1 is a perspective view of an implantable medication infusion pump.
Figure 3:
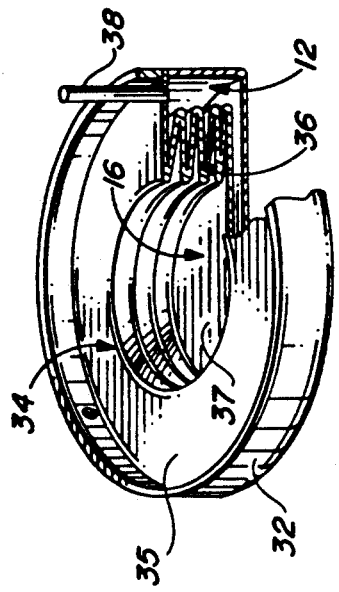
FIG. 3 is an enlarged and fragmented perspective view illustrating a portion of the medication infusion pump deforming a reservoir subassembly which defines a medication chamber and an adjacent pressure reservoir having a pressure fluid therein.
Figure 2:
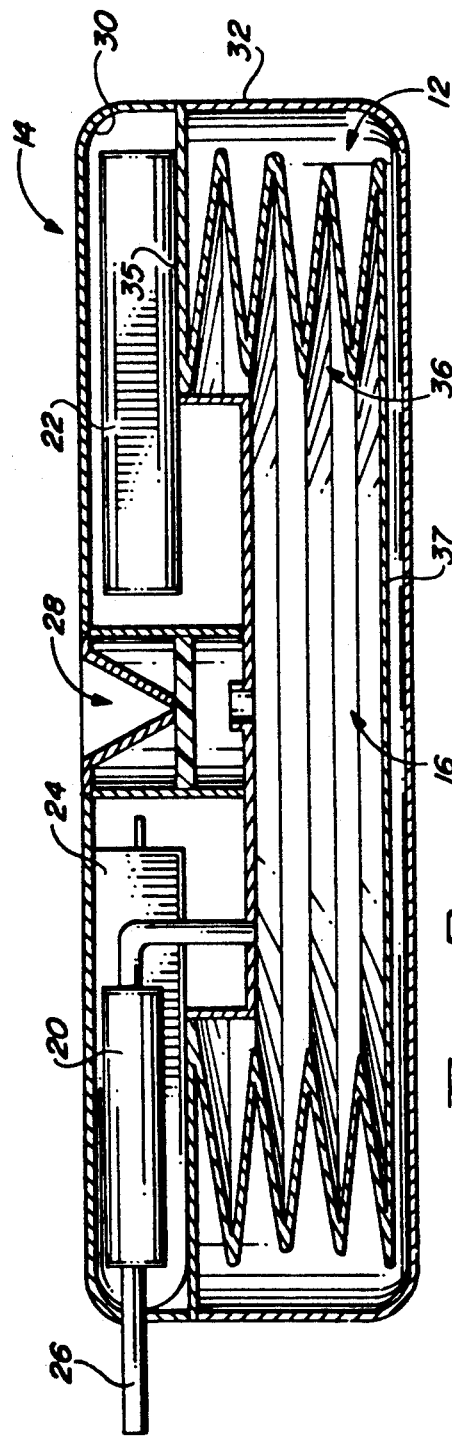
FIG. 2 is an enlarged vertical sectional view of the medication infusion pump, taken generally on the line 2—2 of FIG. 1.

The illustrative medication infusion pump 14 shown in FIGS. 1 through 3 comprises a small and substantially self-contained unit designed for direct implantation into the body of a patient. The pump 14 comprises an hermetically sealed pump housing 18 constructed from a biocompatible material such as titanium or titanium alloy. The assembled pump housing defines the internal medication chamber 16 for receiving and storing the supply of the selected medication in liquid form, such as insulin for a diabetic patient.

The assembled pump housing 18 further encases a miniature dispensing pump 20 and associated electronic control circuitry 22 in combination with a battery 24 for periodically operating the pump 20 to deliver medication doses from the medication chamber 16 to the patient via an appropriate catheter 26 or the like. The control circuitry 22 is suitably preprogrammed to deliver the medication in accordance with individual patient need. An inlet or refill fitting 28 on the pump housing 18 is adapted to receive a hypodermic needle (not shown) to permit percutaneous refilling of the medication chamber 16 without requiring surgical access to the infusion pump. For a more detailed description of the overall construction and operation of implantable infusion pumps of this general type, see U.S. Pat. Nos. 4,373,527 and 4,573,994, both to Fischell, both of which are hereby incorporated herein by reference.

As is known in the art, the infusion pump 14 includes the variable volume pressure reservoir 12 mounted within the pump housing 18 with at least one movable wall of the pressure reservoir 12 being shared with and thereby defining at least a portion of the medication chamber 16. More particularly, the pressure reservoir 12 contains a selected pressure fluid adapted to vary the volumetric size of the medication chamber 16 in accordance with the quantity of medication therein to maintain the medication under substantially constant pressure conditions.

A preferred pressure fluid comprises a fluorocarbon which has a substantially linear pressure characteristic as it changes from liquid to vapor state and vice versa at normal human body temperature and at a normal range of altitudes. A preferred pressure fluid is Freon 113 which assumes a liquid-vapor state at normal body temperature and at altitudinal variations up to about 8,500 feet above sea level to exert a slightly negative and substantially constant pressure of approximately $-1.0$ to $-4.5$ psi on the medication chamber 12.

This slight negative pressure beneficially confines the medication against undesired leakage from the pump housing into the body of the patient. Alternately, other liquid-vapor pressure fluids are known in the art for applying other specific pressures to the medication, such as a slight positive pressure as may be required for some implantable pump designs. In any event, in accordance with primary aspects of the present invention, the improved reservoir filling process and related station apparatus for use in carrying out the process permits the pressure reservoir to be filled with a calibrated quantity of substantially contaminant-free pressure fluid, thereby obtaining significant improvements in operational performance in maintaining the medication under selected and substantially constant pressure conditions. Moreover, the present invention provides means for verifying the performance characteristics of the filled pressure reservoir prior to final assembly of the pump 14.

The illustrative drawings show the assembled pump housing 18 in the form of interfitting upper and lower housing members 30 and 32 of generally circular and shell-shaped configuration. In general terms, the upper housing member 30 has the dispensing pump 20 and the control circuitry 22 with the associated battery 24 installed therein. By contrast, the lower housing member 32 has a bellows unit 34 installed therein. The bellows unit 34 is shown in FIGS. 2 and 3 with an upper ring 35 of generally annular shape having an outer periphery secured in sealed relation to an inboard side of a circular wall on the lower housing member, and an inner periphery joined to a plurality of downwardly extending bellows corrugations referred to generally by the reference numeral 36.

The bellows corrugations 36 are joined in turn to a circular lower plate 37. This structure defines a pump reservoir subassembly with the volumetric space disposed radially within the bellows unit 34 defining the medication chamber 16, and the volumetric space located radially outside and axially below the bellows unit defining the pressure reservoir 12. When the infusion pump is finally assembled, it will be understood that the upper housing member 30 fits over the lower housing member 32 to define and close the upper region of the medication chamber 16 in operative relation with the dispensing pump 20 (FIG. 2).

However, prior to final assembly, an upstanding fill tube 38 (FIG. 3) is mounted on the upper ring 35 of the bellows unit 34 to permit filling of the pressure reservoir 12 with the selected pressure fluid. Moreover, it will also be understood that the bellows unit 34 is typically formed from a metal material adapted for secure and sealed connection to the lower housing member 32, although other materials can be used, and further that the bellows corrugations 36 define the movable wall separating the medication chamber 16 from the pressure reservoir 12.

Figure 4:
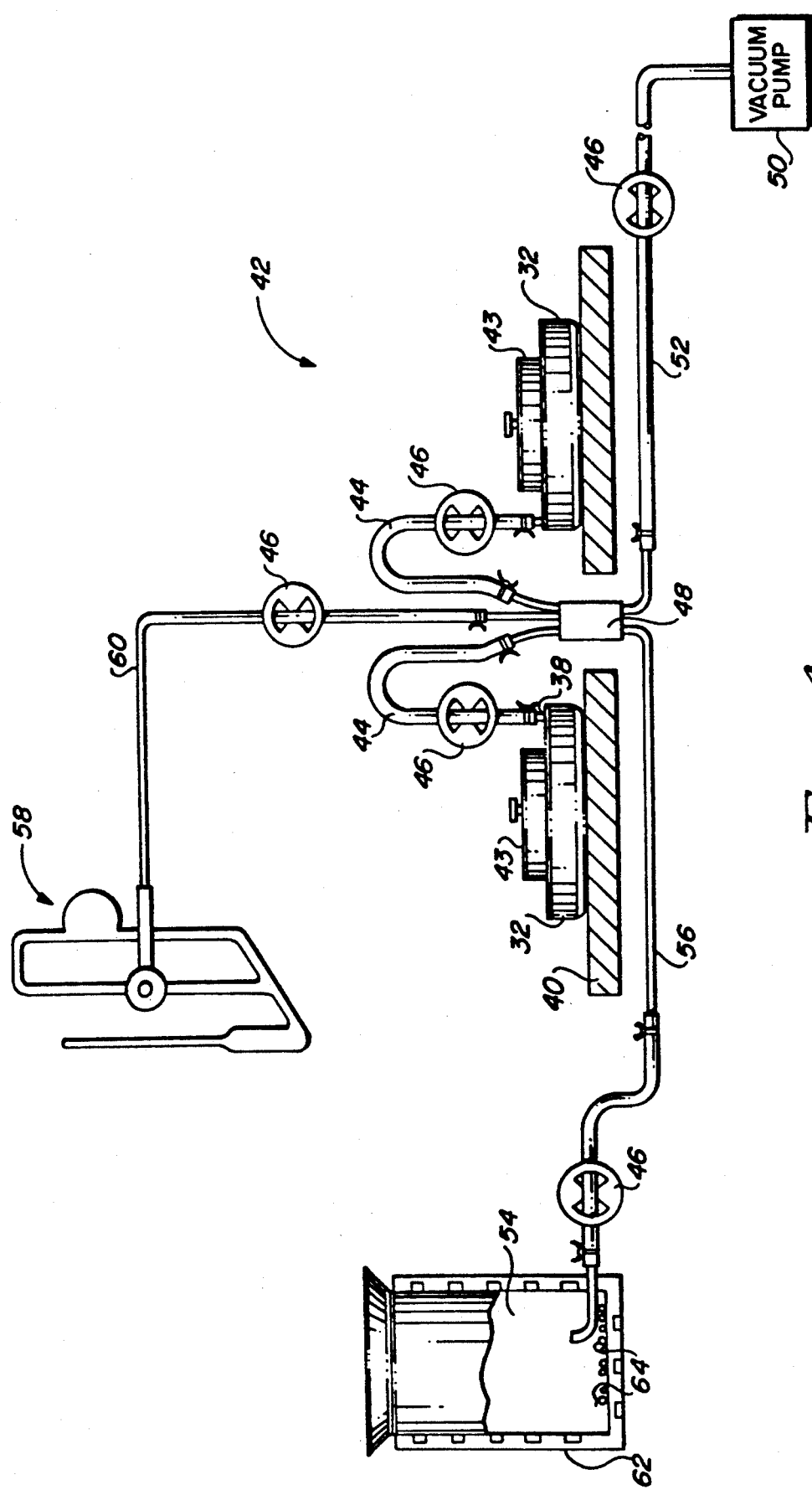
FIG. 4 is a somewhat schematic diagram of a filling station for use in substantially filling the pressure reservoir of the reservoir subassembly with the selected pressure fluid.

As shown in FIG. 4, one or more pump reservoir subassemblies each consisting of a lower housing component 32 and associated bellows unit 34 (not visible in FIG. 4) are placed onto a rack or platform 40 of a filling station 42. A weight 43 is placed onto the lower plate 37 of each bellows unit 34 so that the bellows unit will be fully extended with the associated pressure reservoir 12 at minimum volume. The fill tube 38 of each subassembly is connected via a length of tubing 44 including a clamp 46 to a manifold block 48. The manifold block 48 is adapted in turn to connect the tubing lengths 44 to a vacuum pump 50 via tubing 52, to a supply of selected pressure fluid 54 via tubing 56, and/or to a vacuum gauge 58 via tubing 60. These additional lengths of tubing 52, 56 and 60 each include a clamp 46.

Preliminary to filling of the pressure reservoir of each subassembly, an excess quantity of the selected pressure fluid in liquid form such as Freon 113 is poured into through a sieve to remove moisture into a hopper 62 having conventional boiling chips 64 spread over the bottom thereof. The pressure fluid is then subjected to a low heat of about 120 degrees F. for about five minutes to boil the fluid, while maintaining the clamp 46 on the outlet tubing 56 in a closed condition. This short boiling step has been found to be effective in substantially removing air from the pressure fluid. At the conclusion of the boiling step, the clamp 46 on the tubing 56 is opened briefly to prime the portion of the tubing 56 between the hopper 62 and the clamp 46, and then closed again.

The tubing 52 leading to the vacuum pump 50 is then opened by manipulation of the clamp 46, and the vacuum pump 50 is energized to draw a vacuum within the tubing network. During this pump operation step, the clamps 46 on the segments of tubing 44 associated with the subassembly fill tubes 38 are opened to permit a vacuum to be drawn in each pressure reservoir 12. In addition, the clamp 46 associated with the tubing 60 leading to vacuum gauge 58 is opened so that the magnitude of the drawn vacuum can be observed. A drawn vacuum level on the order of at least about 1 mm Hg is preferred.

When the desired vacuum level is achieved, the vacuum pump tubing 52 and the vacuum gauge tubing 60 are closed with the clamps 46. The tubing 56 associated with the hopper 62 is then immediately opened to allow the pressure fluid to be drawn by the vacuum through the tubing network to fill the pressure reservoir 12 of each pump subassembly. To achieve the desired vacuum-drawn flow, the hopper 62 should be located at approximately the same vertical height position as the subassemblies. When the pressure reservoirs of the subassemblies are filled with pressure fluid, the clamps 46 on the fill tubing 44 are closed and the weights 43 are removed, and the subassemblies are removed from the fill station.

Each pump reservoir subassembly is transferred to a calibration station 66, as depicted in FIG. 5. The objective of the calibration station 66 is to ensure that the amount of pressure fluid sealed in the pressure reservoir is precisely calibrated for the particular device being assembled. Too much fluid in the pressure chamber can cause problems with nucleation of the fluid when the reservoir is fully filled to capacity, reducing the volume of the pressure chamber to its minimum size. On the other hand, too little fluid in the pressure reservoir will not provide sufficient pressure (be it either positive or negative) on the medication chamber wall shared in common with the pressure chamber. Thus, the calibration station 66 is used to precisely calibrate the amount of pressure fluid sealed in the pressure reservoir.

The calibration station 66 includes a base 68 for seated support of the subassembly. A seal plate 70 is placed over the upper ring 35 of the bellows unit and is securely retained thereon by a lock screw 72 threaded through an upper support bar 74 of the station. The seal plate 70 closes and seals the otherwise upwardly open medication chamber 16. An inlet tube 76 mounted on the seal plate 70 permits introduction of a calibration fluid from a supply 78 through a length of tubing 80.

The calibration fluid, which may be nitrogen gas, fills the medication chamber 16 of the subassembly at a predetermined pressure level, such as about 10 psi, as indicated on a suitable gauge 82. The clamp 46 on the fill tubing 44 is then opened whereby a portion of the pressure fluid in the pressure reservoir 12 is expelled to a suitable container 84. Accordingly, the positive pressure supplied to the medication chamber causes the medication chamber to expand and thereby reduce the volumetric size of the pressure reservoir.

Although the specific positive pressure used for this calibration step may vary, the result is that the quantity of pressure fluid within each pump is calibrated for uniform performance characteristics. The clamp 46 on the tubing 44 is then tightly closed and the subassembly is removed from the calibration station 66. The pressure reservoir 12 of the subassembly is closed and sealed by pinch welding or another suitable welding step applied to the fill tube 38, while taking appropriate steps to ensure that the pressure fluid is not exposed to the atmosphere.

Following the calibration step, the filled subassembly is subjected to performance testing under simulated implantation conditions prior to final assembly with other components of the infusion pump. This performance testing step beneficially permits those units which exhibit unsatisfactory performance characteristics to be identified and/or reworked as needed. In this regard, performance testing is carried out by monitoring the quantity of liquid which must be withdrawn from a completely filled medication chamber 16 before the chamber 16 is subjected to the desired and substantially constant design pressure as applied by the pressure fluid in liquid-gas phase within the pressure reservoir 12.

As a general proposition, a leak-free pressure reservoir filled with substantially contaminant-free pressure fluid will apply the design pressure to the medication chamber when a relatively small quantity of liquid has been withdrawn from a fully filled medication chamber, in contrast with a requirement that a larger quantity of liquid must be withdrawn from the medication chamber to achieve the design pressure when the pressure fluid includes undesirable levels of contaminants. The use of a relatively contaminant-free pressure fluid therefore maximizes the available volume of the medication chamber 16 to correspondingly and desirably maximize the medication-containing capacity of the infusion pump 14.

The performance test station 86 as shown in FIG. 6 to include on upwardly open tray 88 filled with a fluid such as water 90 at ambient pressure and at a temperature substantially equal to the body temperature to which an implanted pump would be subjected. The medication chamber 16 is also filled with the same liquid and closed by means of a clamp plate 92 or the like seated onto the upper ring 35 of the bellows unit 34.

A pipette 94 extends through the clamp plate 92 to a piston assembly 96 including a manually reciprocative piston 98 within a transparent or translucent cylinder 100. The pipette 94 and the cylinder 100 are primed with the liquid disposed within the medication chamber 16. A pressure tap line 102 connects with the pipette 94 to communicate line pressure to a transducer 104 associated with a display 206 to permit the pressure to be measured and monitored.

With the medication chamber 16 fully filled with the liquid and the pressure display 106 reading a chamber pressure level of essentially zero or atmospheric pressure, the piston 98 is retracted within the cylinder 100 to withdraw liquid from the medication chamber. As this withdrawal step proceeds, the volumetric quantity of withdrawn liquid can be monitored by observing the piston position relative to gradation markings 108 on the cylinder. As noted above, withdrawal of a small quantity of liquid from the medication chamber 16 permits the pressure fluid within the pressure reservoir 12 to impose a pressure on the medication chamber.

When the pressure fluid is substantially free of contaminants, the design pressure will be imposed on the medication chamber and viewed on the display 106, when a small quantity of liquid has been withdrawn therefor, such as a quantity of about 1 or 2 cubic centimeters (cc's) from a medication chamber having a capacity of about twenty cc's. Alternately, if the pressure fluid contains substantial contaminant levels, the design pressure may not be reached until perhaps seven to ten cc's have been withdrawn. The performance characteristics of each subassembly can thus be evaluated through the use of the performance test station 86 to identify faulty units before final assembly and/or implantation.

The improved pressure reservoir filling process and related station apparatus of the present invention thus enables accurate and reliable pressure reservoir filling and subsequent performance testing prior to implantation into a patient.

Although an exemplary embodiment of the present invention has been shown and described, it will be apparent to those having ordinary skill in the art that a number of changes, modifications, improvements, or alterations to the invention as described herein may be made, none of which depart from the spirit of the present invention. All such changes, modifications, and alterations should therefore be seen as within the scope of the present invention. Accordingly, no limitation on the invention is intended by way of the foregoing description and the accompanying drawings, except as set forth in the appended claims.

What is claimed is:

1. A method of filling a pressure reservoir of an implantable medication infusion pump with a selected pressure fluid, wherein the pressure reservoir is separated from a medication chamber by a movable wall, said method comprising the steps of:
   drawing a vacuum in the pressure reservoir;
   connecting the pressure reservoir to a supply of the pressure fluid to vacuum-draw the pressure fluid for flow into and to fill the pressure reservoir;
   calibrating the quantity of the pressure fluid within the pressure reservoir by subjecting the pressure reservoir to a predetermined pressure to expel excess pressure fluid therefrom and to calibrate the quantity of pressure fluid therein;
   sealing the pressure reservoir; and
   performance testing the pressure reservoir under simulated implantation conditions.

2. A method as defined in claim further comprising:
   the step of retaining the pressure reservoir in a substantially minimum volume configuration during said step of connecting the pressure reservoir to the supply of pressure fluid.

3. A method as defined in claim 1, wherein said connecting step comprises:
   connecting the pressure reservoir to the supply of pressure fluid in liquid form.

4. A method as defined in claim 3, further comprising:
   the step of expanding the volume of the medication chamber to decrease and retain the volume of the pressure reservoir at a substantially minimum volume configuration during said step of connecting the pressure fluid.

5. A method as defined in claim 4, wherein the pressure fluid is a selected fluorocarbon.

6. A method as defined in claim 5, further comprising: the step of removing contaminants from the pressure fluid prior to connecting the supply of the pressure fluid to the pressure reservoir.

7. A method as defined in claim 6, wherein said contaminant removal step comprises boiling the fluorocarbon pressure fluid.

8. A method as defined in claim wherein said calibrating step comprises:
filling the medication chamber with a selected calibration fluid at a predetermined pressure level.

9. A method as defined in claim 1, wherein said calibrating step comprises:
filling the medication chamber with a selected gas at a predetermined positive pressure level.

10. A method as defined in claim 1, wherein said performance testing step comprises:
immersing the pressure reservoir in a bath of liquid at a temperature generally corresponding to patient body temperature;
filling the medication chamber with liquid;
withdrawing a small quantity of the liquid from the medication chamber; and
monitoring the pressure of the liquid within the medication chamber in relation to the quantity of liquid withdrawn therefrom to determine pressure reservoir performance.

11. A method of filling a pressure reservoir of a reservoir subassembly with a selected pressure fluid, said subassembly having the pressure reservoir separated from a medication chamber by a movable wall and being adapted for use in an implantable medication infusion pump, said method comprising the steps of:
drawing a vacuum in the pressure reservoir;
filling the pressure reservoir with the pressure fluid in liquid form by connecting the pressure reservoir to a supply of the pressure fluid for vacuum-drawn flow into and to fill the pressure reservoir, said filling step including retaining the pressure reservoir in a substantially minimum volume configuration;
calibrating the quantity of the pressure fluid within the pressure reservoir by filling the medication chamber with a calibration fluid under predetermined pressure to expel excess pressure fluid from the pressure reservoir;
closing the pressure reservoir; and
performance testing the pressure reservoir under simulated implantation conditions, said performance testing step comprising:
immersing the pressure reservoir in a bath of liquid at a temperature generally corresponding to patient body temperature;
filling the medication chamber with liquid;
withdrawing a small quantity of the liquid from the medication chamber; and
monitoring the pressure of the liquid within the medication chamber in relation to the quantity of liquid withdrawn therefrom to determine pressure reservoir performance.

12. A method as defined in claim wherein the pressure fluid is a selected fluorocarbon.

13. A method as defined in claim 12, further comprising:
the step of removing contaminants from the pressure fluid prior to connecting the supply of the pressure fluid to the pressure reservoir.

14. A method as defined in claim 13, wherein said contaminant removal step comprises boiling the fluorocarbon pressure fluid.

15. A method of filling a pressure reservoir of an implantable medication infusion pump with a selected pressure fluid, wherein the pressure reservoir is separated from a medication chamber by a movable wall, said method comprising the steps of:
drawing a vacuum in the pressure reservoir;
connecting the pressure reservoir to a supply of the pressure fluid to vacuum-draw the pressure fluid for flow into and to fill the pressure reservoir;
calibrating the quantity of the pressure fluid within the pressure reservoir by subjecting the pressure reservoir to a predetermined pressure to expel excess pressure fluid therefrom and to calibrate the quantity of pressure fluid therein; and
sealing the pressure reservoir.

16. Station apparatus for filling a pressure reservoir of an implantable medication infusion pump with a selected pressure fluid, wherein the pressure reservoir is separated from a medication chamber by a movable wall, said station apparatus comprising:
means for drawing a vacuum in the pressure reservoir;
means for connecting the pressure reservoir to a supply of the pressure fluid to vacuum-draw the pressure fluid for flow into and to fill the pressure reservoir;
means for calibrating the quantity of the pressure fluid within the pressure reservoir by subjecting the pressure reservoir a predetermined pressure to expel excess pressure fluid therefrom and to calibrate the quantity of pressure;
means for sealing the pressure reservoir; and
means for performance testing the pressure reservoir under simulated implantation conditions.

17. The station apparatus of claim 16 further comprising:
means for retaining the pressure reservoir in a substantially minimum volume configuration during vacuum-draw filling of the pressure reservoir with the pressure fluid.

18. A station apparatus as defined in claim 16, wherein said vacuum drawing means comprises a vacuum pump, and further comprising:
a manifold block;
tubing means for connecting said manifold block with said supply of pressure fluid, with said vacuum pump, and with said pressure reservoir; and
tubing clamp means for controlling fluid flow through said tubing means.

19. A station apparatus as defined in claim 16, further comprising:
means for expanding the volume of the medication chamber to decrease and retain the volume of the pressure reservoir at a substantially minimum volume configuration during filling of said pressure reservoir with the pressure fluid.

20. A station apparatus as defined in claim 19, wherein the pressure fluid is a selected fluorocarbon.

21. A station apparatus as defined in claim 16, wherein said calibrating means comprises:

means for filling the medication chamber with a selected calibration fluid at a predetermined pressure level.

22. A station apparatus as defined in claim 16, wherein said performance testing means comprises:
   means for immersing the pressure reservoir in a bath of liquid at a temperature generally corresponding to patient body temperature;
   means for filling the medication chamber with a liquid;
   means for withdrawing a small quantity of the liquid from the medication chamber; and
   means for monitoring the pressure of the liquid within the medication chamber in relation to the quantity of liquid withdrawn therefrom to determine pressure reservoir performance.

23. Station apparatus for filling a pressure reservoir of an implantable medication infusion pump with a selected pressure fluid, wherein the pressure reservoir is separated from a medication chamber by a movable wall, said station apparatus comprising:
   means for drawing a vacuum in the pressure reservoir;
   means for connecting the pressure reservoir to a supply of the pressure fluid to vacuum-draw the pressure fluid for flow into and to fill the pressure reservoir;
   means for calibrating the quantity of the pressure fluid within the pressure reservoir by subjecting the pressure reservoir to a predetermined pressure to expel excess pressure fluid therefrom and to calibrate the quantity of pressure fluid, and
   means for sealing the pressure reservoir.

* * * * *